(12) United States Patent
Wilbertz et al.

(10) Patent No.: US 9,500,620 B2
(45) Date of Patent: Nov. 22, 2016

(54) LAYER SYSTEM

(71) Applicant: Micronas GmbH, Freiburg (DE)

(72) Inventors: Christoph Wilbertz, Gundelfingen (DE); Dominik Zimmermann, Freiburg (DE)

(73) Assignee: Micronas GmbH, Freiburg (DE)

( * ) Notice: Subject to any disclaimer, the term of this patent is extended or adjusted under 35 U.S.C. 154(b) by 0 days.

(21) Appl. No.: 14/507,428

(22) Filed: Oct. 6, 2014

(65) Prior Publication Data

US 2015/0096354 A1    Apr. 9, 2015

(30) Foreign Application Priority Data

Oct. 5, 2013  (DE) .......................... 10 2013 016 331

(51) Int. Cl.
*G01N 27/403*    (2006.01)
*G01N 27/414*    (2006.01)

(52) U.S. Cl.
CPC ....... *G01N 27/4143* (2013.01); *G01N 27/4146* (2013.01); *Y10T 428/24802* (2015.01); *Y10T 428/24926* (2015.01)

(58) Field of Classification Search
CPC .................. H01L 2924/0002; H01L 2924/00; H01L 21/02063; H01L 21/28506; H01L 21/28518; H01L 21/30608; H01L 21/31637; H01L 21/3205; H01L 23/4827; H01L 28/56; H01L 2924/3011; H01L 29/66; H01L 31/0236

See application file for complete search history.

(56) References Cited

U.S. PATENT DOCUMENTS

| | | | |
|---|---|---|---|
| 4,137,123 A * | 1/1979 | Bailey ............... | H01L 21/30608 136/256 |
| 4,952,904 A | 8/1990 | Johnson et al. | |
| 7,459,732 B2 | 12/2008 | Fleischer et al. | |
| 8,899,098 B2 | 12/2014 | Senft et al. | |
| 2007/0181426 A1 * | 8/2007 | Fleischer ........... | G01N 27/4141 204/431 |
| 2010/0154875 A1 * | 6/2010 | Borland ............ | H01L 21/28537 136/255 |
| 2010/0200059 A1 * | 8/2010 | Lu ....................... | H01L 31/0749 136/256 |
| 2011/0117738 A1 * | 5/2011 | Russell ................... | C23C 14/02 438/664 |

(Continued)

FOREIGN PATENT DOCUMENTS

| | | |
|---|---|---|
| DE | 38 04 683 A1 | 8/1988 |
| DE | 44 44 607 A1 | 5/1996 |
| DE | 689 24 140 T2 | 5/1996 |

(Continued)

OTHER PUBLICATIONS

Zhu et al., "Dual functions of anti-reflectance and surface passivation of the atomic layer deposited $Al_2O_3$ films on crystalline silicon substrates," http://arxiv.org/ftp/arxiv/papers/1207/1207.0619.pdf, pp. 1-14 (Jul. 3, 2012).

(Continued)

*Primary Examiner* — Robert Bachner

(74) *Attorney, Agent, or Firm* — Muncy, Geissler, Olds & Lowe, P.C.

(57) ABSTRACT

A layer system having a layer region, whereby the layer region has a single-crystal silicon substrate with a front side and a back side, and whereby a textured surface is formed on the front side and the textured surface has a topography with different heights and a thin film layer of a metal oxide and/or an oxide ceramic is formed on the textured surface, whereby the thin film layer covers the textured surface only partially.

22 Claims, 3 Drawing Sheets

(56) References Cited

U.S. PATENT DOCUMENTS

2012/0272720 A1* 11/2012 Wiesner ............... G01N 27/12
73/31.05
2013/0061924 A1* 3/2013 Munzer ........... H01L 31/022425
136/259

FOREIGN PATENT DOCUMENTS

| DE | 10 2012 022 136 A1 | 5/2013 |
| EP | 1 707 952 A1 | 10/2006 |
| EP | 2 372 355 A2 | 10/2011 |
| WO | WO 2004/032197 A2 | 4/2004 |

OTHER PUBLICATIONS

Wollenstein et al., "Cobalt oxide based gas sensors on silicon substrate for operation at low temperatures," Sensors and Actuators B, vol. 93, pp. 442-448 (Aug. 1, 2003).

Gergintschew et al., "The capacitively controlled field effect transistor (CCFET) as a new low power gas sensor," Sensors and Actuators B, vol. 36, pp. 285-289 (May 23, 2013).

* cited by examiner

LAYER SYSTEM

This nonprovisional application claims priority under 35 U.S.C. §119(a) to German Patent Application No. 10 2013 016 331.5, which was filed in Germany on Oct. 5, 2013, and which is herein incorporated by reference.

BACKGROUND OF THE INVENTION

Field of the Invention

The invention relates to a layer system.

Description of the Background Art

DE 689 24 140 T2, which corresponds to U.S. Pat. No. 4,952,904, and discloses a thin film sensor structure with platinum on silicon nitride, whereby the thin film layer of metal oxide is arranged on the silicon nitride layer and the thin film layer is covered with platinum. A method for preparing textured silicon is known from U.S. Pat. No. 4,137,123 B. In this case, the surface is treated with a dilute KOH etching in order to reduce the reflectivity of the surface.

Further, EP 1 707 952 A1, which corresponds to U.S. Pat. No. 7,459,732, which is herein incorporated by reference, and which discloses a layer system integrated into a gas sensor.

SUMMARY OF THE INVENTION

It is therefore an object of the invention to provide a device that refines the conventional art.

According to an embodiment of the invention, a layer system is provided having a layer region, whereby the layer region has a single-crystal silicon substrate with a front side and a back side, and whereby a textured surface is formed on the front side and the textured surface has a topography with different heights and a thin film layer of a metal oxide and/or an oxide ceramic is formed on the textured surface, whereby the thin film layer covers the textured surface only partially. It should be noted that because of the texture, the surface has a microroughness and the thin film layer adapts to the surface of the texture, preferably conformally, but the peaks of the texture are not covered. It should be noted further that the silicon substrate is preferably formed as a semiconductor wafer. Integrated circuits are formed on such silicon wafers. Preferably, precisely the same semiconductor wafers are used for the formation of the textured surface as in the case of the production of an integrated circuit.

An advantage of the device of the invention is that the silicon substrate with the textured surface has such a surface roughness that the thin film layer has a frictional connection with the support. This makes it possible to join the brittle thin film layers to the silicon surface without an adhesive bond. A further advantage is that the thin film layers have a large surface. It is preferred hereby that the thin film layer has a thickness smaller than the texturing depth.

Tests by the applicant have shown that it is advantageous if the textured surface has a pyramid-shaped topography. In a preferred embodiment, the side surfaces of the pyramid-shaped texture are formed as 111 surfaces. Further, the texture on the top side has 100 surfaces. Such a pyramid-shaped topography can be produced with a KOH etching.

In an embodiment, the textured surface has peaks with no thin film layer and/or plateaus with no thin film layer, whereby the peaks with no thin film layer and/or plateaus with no thin film layer project above the surface of the thin film layer.

In a further embodiment, the thin film layer comprises a catalyst. Tests have shown that it is advantageous to use platinum and/or palladium and/or rhodium as a catalyst.

In an embodiment, at least one metallically conductive intermediate layer can be formed between the thin film layer and the textured surface and the textured surface can be partially or completely covered by the metallically conductive intermediate layer. It is understood that the one or more intermediate layers form a material bonding connection with the surface of the silicon substrate on the surface of the silicon substrate and accordingly the thin film layer forms a material bonding connection with the topmost intermediate layer. Accordingly, a sequence of at least two layers is formed on the textured surface of the silicon substrate.

In an embodiment, the metallically conductive intermediate layer comprises a silicide layer, whereby it is preferred that the silicide layer comprises platinum and/or titanium and/or palladium. In a further embodiment, the metallically conductive intermediate layer is electrically connected. In an embodiment, the thin film layer is electrically connected in addition to or instead of the intermediate layer.

The textured silicon can have a p- or an n-type doping in the layer region. It is preferable for this purpose to form an n- or p-well in the layer region.

It is advantageous to integrate the layer region into an SGFET or a CCFET gas sensor as a gas-sensitive control electrode. Further, it has proven advantageous to make the thin film layer of gallium oxide and/or tin oxide and/or barium titanate and/or barium carbonate.

The textured surface can contain pyramid top surfaces or pyramid peaks and a distance of 1 μm to 10 μm is formed between directly adjacent pyramid peaks or pyramid top surfaces and the pyramid top surfaces or pyramid peaks are between 1 μm and 10 μm in height.

In an embodiment, the metallic intermediate layer has a texturing with a texture spacing of 0.1 μm to 1 μm and a texture depth of 0.1 μm to 1 μm, whereby the texture spacing and the texture depth are in each case smaller than those of the surface of the silicon layer.

In an embodiment, the thin film layer is formed polycrystalline and the grain sizes of the thin film layer are smaller than 2 μm.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

DETAILED DESCRIPTION

Figure 1A:
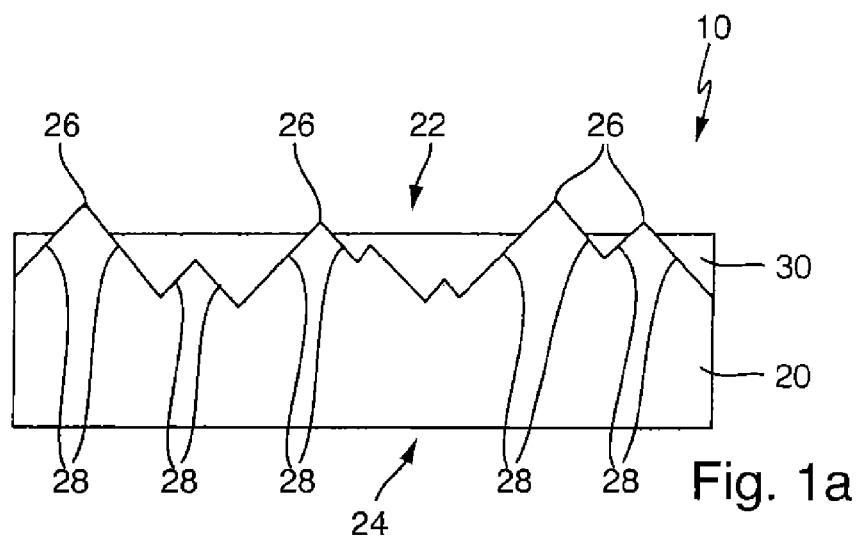
FIG. 1a shows a cross-sectional view of an embodiment of the invention of the layer structure.

The illustration in FIG. 1a shows a cross-sectional view of a first embodiment of a layer system 10, having a single-crystal silicon substrate 20, with a front side 22 and a back side 24. A textured surface is formed on front side 22 of silicon substrate 20. In this regard, the textured surface has a topography with different heights. It should be noted that the topography shows a plurality of raised areas, whereby, for reasons of clarity, the raised areas are shown simplified as peaks 26. As the texture is produced preferably by means of KOH etching, the topography of the textured surface is pyramid-shaped; i.e., side surfaces 28 of the pyramid-shaped raised areas or peaks 26 are formed as 111 surfaces. Provided the raised areas of the texture form the plateaus, 100 surfaces (not shown) are formed on the top side. It should be noted further that the peaks have different heights. Furthermore, the peaks have different distances to one another. It is preferable that a distance of 1 μm to 10 μm is formed between directly adjacent pyramid peaks or pyramid top surfaces, and the pyramid top surfaces or pyramid peaks have a height between 1 μm and 10 μm with regard to the base of the pyramid. Further, silicon substrate 20, which is generally formed as a front side of a silicon semiconductor wafer, has an n- or p-type dopant concentration, preferably of phosphorus or boron, in a range of several $10e17$ $N/cm^3$ to a few $10e19$ $N/cm^3$. It is understood that the single-crystal layer can also be grown epitaxially. Silicon substrate 20 is connected electrically in addition to or instead of thin film layer 30 (this is not shown). It should be noted further that apart from the shown textured regions on silicon substrate layer 20, non-textured regions (not shown) can also be formed. Known photolithographic methods are used in order to separate such regions from one another.

A thin film layer 30 of a metal oxide and/or an oxide ceramic is formed on the textured surface, whereby thin film layer 30 covers the textured surface only partially and preferably contains gallium oxide and/or tin oxide and/or barium titanate and/or barium carbonate. It is advantageous in addition, if thin film layer 30 comprises a catalyst. It is especially advantageous, if the catalyst includes platinum and/or palladium and/or rhodium. Thin film layer 30 has a conductivity in the region of the metals. Further, the thin film layer is connected electrically.

It is preferred that thin film layer 30 at the thickest location has a thickness smaller than 10 μm, but a part of peaks 26 or of the plateaus projects above the surface of thin film layer 30 and is not covered by thin film layer 30. Preferably, thin film layer 30 forms a material bonding connection with the support. It is advantageous if the thin film layer is formed polycrystalline and the grain sizes of the thin film layer are smaller than 2 μm.

Figure 1B:
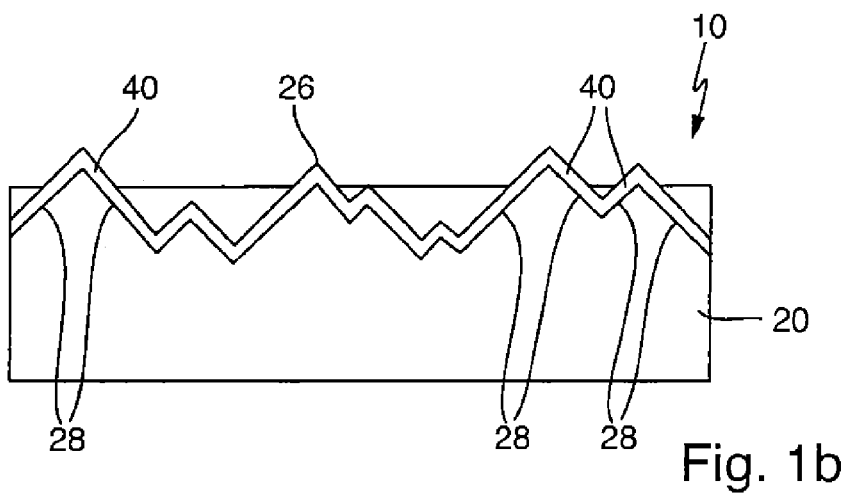
FIG. 1b shows a cross-sectional view of an embodiment of the invention of the layer structure.

In the illustration of FIG. 1b, a cross-sectional view of a second embodiment of layer system 10 is shown. Only the differences to the explanations in relation to FIG. 1a will be indicated hereafter. A metallically conductive intermediate layer 40 is formed between thin film layer 30 and the surface on front side 22 of silicon substrate 20. Intermediate layer 40 covers the surface, therefore also the peaks of silicon substrate 20, preferably completely and conformally. Intermediate layer 40, on the one hand, forms a material bonding connection with the support, therefore with the surface of silicon substrate layer 20, and also a material bonding connection with thin film layer 30 lying on intermediate layer 40.

It is understood that the metallically conductive intermediate layer 40 is connected electrically (not shown). The electrical connection of intermediate layer 40 can be formed in addition or alternatively to the electrical connections of silicon substrate 20 and/or thin film layer 30. The electrical connection can be formed in the textured or, if present, non-textured regions of silicon substrate 20. Preferably, the metallically conductive intermediate layer comprises a silicide layer of platinum and/or tungsten and/or titanium and/or palladium.

Figure 1C:
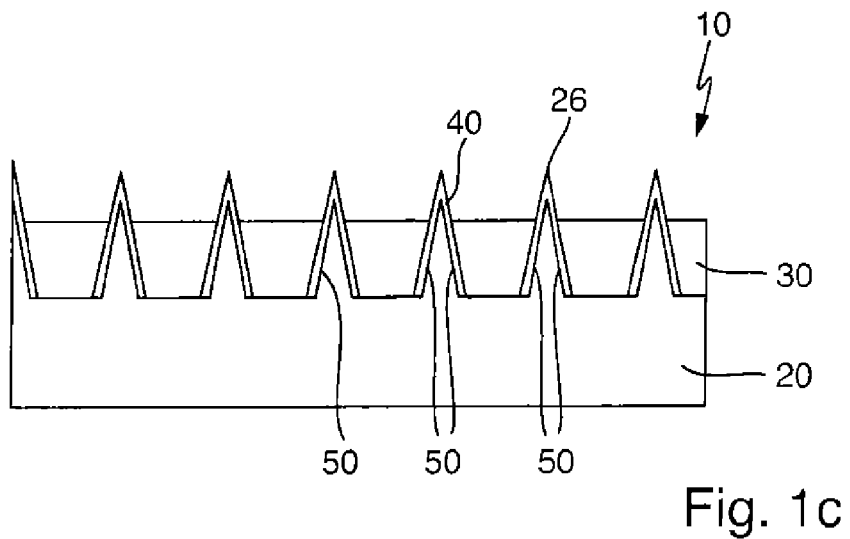
FIG. 1c shows a cross-sectional view of an embodiment of the invention of the layer structure.

In the illustration of FIG. 1c, a cross-sectional view of a third embodiment of layer system 10 is shown. Only the differences to the explanations in relation to FIG. 1b will be indicated hereafter. The texturing of the surface of silicon substrate 20 now forms a regular topography. Peaks 26, spaced uniformly apart, project from the surface of silicon substrate 20. The side surfaces of the peaks are not necessarily formed from 111 surfaces. In particular, photolithographic methods, i.e., mask processes in conjunction with dry etching, are used to produce peaks 26.

Figure 2:
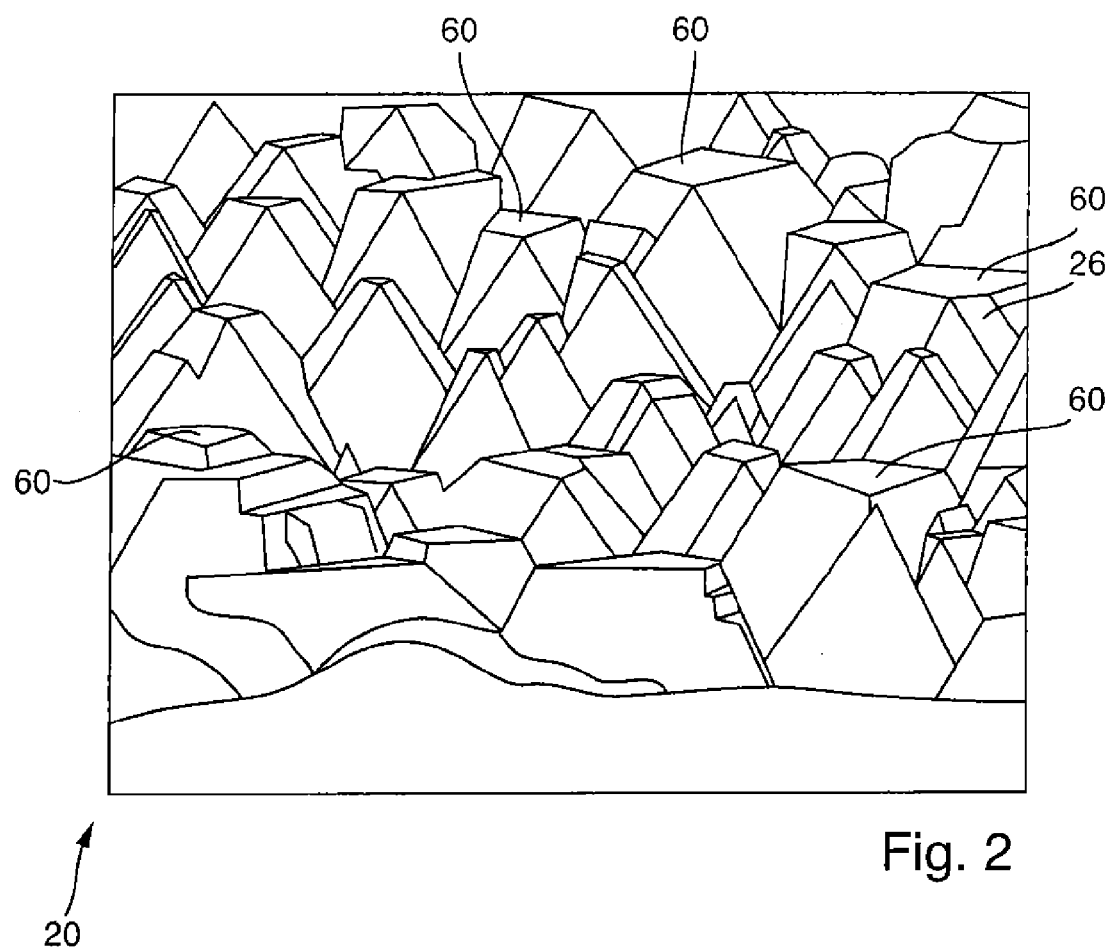
FIG. 2 shows an electron micrograph of a textured surface on a silicon substrate.

In the illustration of FIG. 2, an electron micrograph of a textured surface of silicon substrate 20 is shown immediately after the KOH etching. As a result, both thin film layer 30 and intermediate layer 40 are absent. Only the differences to the explanations in relation to FIG. 1a will be indicated hereafter. The pyramid-shaped structure is evident, whereby now also plateaus 60 of different sizes are formed apart from the peaks.

Figure 3:
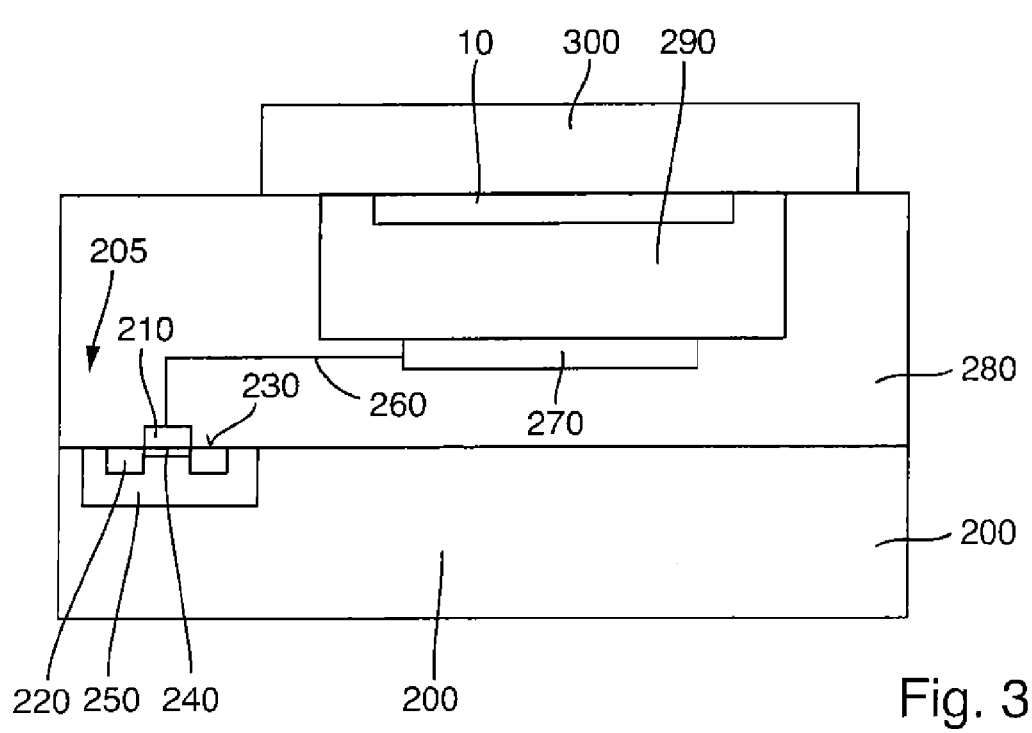
FIG. 3 shows a basic sketch of a CCFET transistor with use of an electrode with a layer structure according to one of the embodiments shown in FIG. 1a-FIG. 1c.

In the illustration of FIG. 3, a basic sketch of a CCFET transistor is shown with use of an electrode with a layer structure of one of the embodiments in one of FIGS. 1a-1c. Only the differences to the explanations in relation to the illustrations in the previous figures will be indicated below. A MOS transistor 205 with a gate 210, a source 220, and a drain 230 is formed in the top side of a silicon wafer 200. A channel region 240 is arranged between source 220 and drain 230. MOS transistor 205 is arranged in a well 250. Gate 210 is connected by a line 260 to a first electrode 270. A multiple-layer dielectric layer structure 280 is arranged on the top side of silicon wafer 200. Layer structure 280 forms a cavity 290. First electrode 270 is arranged on the bottom surface of cavity 290. The cavity is covered by a support structure 300. Support structure 300 has layer system 10 on its bottom side, whereby the surface of silicon substrate 20 points downward in the direction of first electrode 270. Layer system 10 forms a counter electrode to first electrode 270. Both electrodes together form a capacitor. Provided thin film layer 30 has gas-sensitive properties, the potential at the surface, facing cavity 290, of layer system 10 of the capacitor changes depending on the accumulation of specific gas molecules, and the conductivity of channel region 240 changes as a result. In summary, layer system 10 is integrated as a gas-sensitive control electrode in a CCFET gas sensor.

Figure 4:
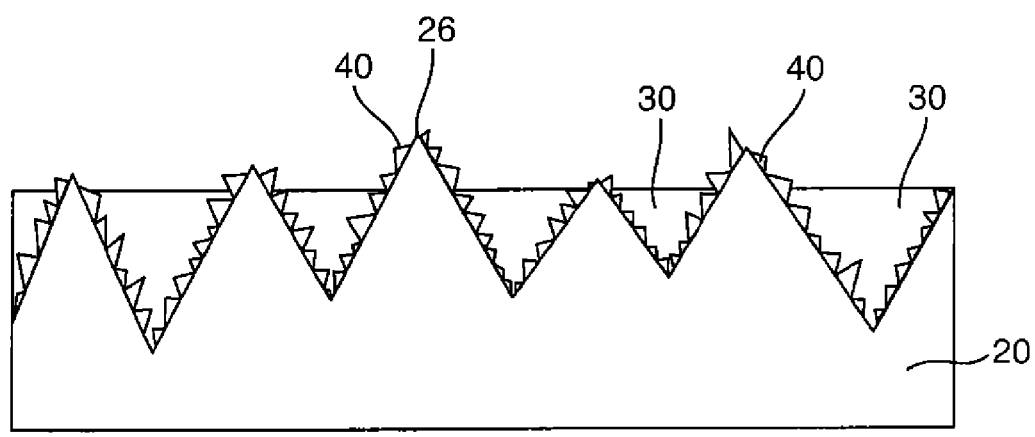
FIG. 4 shows a cross-sectional view of a fourth embodiment of the invention of the layer structure with a textured intermediate layer.

A cross-sectional view of a fourth embodiment of the invention of the layer structure with a textured intermediate layer is shown in the illustration of FIG. 4. Only the differences to the explanations in relation to the illustration of the embodiment of FIG. 1b will be indicated. Intermediate layer 40 also has texturing, whereby the texture spacing is preferably between 0.1 μm to 1 μm and the texture depth is preferably between 0.1 μm to 1 μm. In any event, the texture spacing and the texture depth are in each case smaller than the texture spacing and the texture depth of the surface of silicon substrate 20.

The invention being thus described, it will be obvious that the same may be varied in many ways. Such variations are not to be regarded as a departure from the spirit and scope of the invention, and all such modifications as would be obvious to one skilled in the art are to be included within the scope of the following claims.

What is claimed is:

1. A layer system having a layer region, the layer region comprising:
   a single-crystal silicon substrate with a front side and a back side;
   a textured surface formed on the front side, the textured surface having a topography with different heights; and
   a thin film layer of a metal oxide and/or an oxide ceramic formed on the textured surface, the thin film layer formed such that a top portion of exposed peaks or plateaus is not covered by the thin film layer, the thin film layer disposed between adjacent exposed peaks or plateaus,
   wherein the adjacent exposed peaks or plateaus are higher than a flat surface of the thin film layer, the flat surface being substantially parallel to the back side of the substrate.

2. The layer system according to claim 1, wherein the textured surface has a pyramid-shaped topography.

3. The layer system according to claim 1, wherein exposed peaks with no thin film and/or plateaus with no thin film project above the flat surface of the thin film layer.

4. The layer system according to claim 1, wherein the thin film layer comprises a catalyst.

5. The layer system according to claim 4, wherein the catalyst has platinum and/or palladium and/or rhodium.

6. The layer system according to claim 1, wherein the thin film layer has a thickness smaller than 10 µm.

7. The layer system according to claim 1, wherein a metallically conductive intermediate layer partially or completely covers the textured surface between the thin film layer and the textured surface.

8. The layer system according to claim 7, wherein the metallically conductive intermediate layer comprises a silicide layer.

9. The layer system according to claim 8, wherein the silicide layer comprises platinum and/or titanium and/or palladium.

10. The layer system according to claim 7, wherein the metallically conductive intermediate layer is electrically connectable.

11. The layer system according to claim 1, wherein the thin film layer is electrically connectable.

12. The layer system according to claim 1, wherein the textured silicon substrate has a p- or an n-type doping in the layer region.

13. The layer system according to claim 1, wherein the layer region is integrated in an SGFET or CCFET gas sensor as a gas-sensitive control electrode.

14. The layer system according to claim 2, wherein side surfaces of the pyramid-shaped topography are 111 surfaces and the textured surface on a top side has 100 surfaces.

15. The layer system according to claim 1, wherein the thin film layer contains gallium oxide and/or tin oxide and/or barium titanate and/or barium carbonate.

16. The layer system according to claim 7, wherein the textured surface contains pyramid top surfaces or pyramid peaks and a distance of 1 µm to 10 µm is formed between directly adjacent pyramid peaks or pyramid top surfaces and the pyramid top surfaces or pyramid peaks are between 1 µm and 10 µm in height.

17. The layer system according to claim 7, wherein the metallic intermediate layer has a texturing with a texture spacing of 0.1 µm to 1 µm and a texture depth of 0.1 µm to 1 µm and the texture spacing and the texture depth are in each case smaller than those at the surface of the silicon substrate.

18. The layer system according to claim 1, wherein the thin film layer is formed polycrystalline and the grain sizes of the thin film layer are smaller than 2 µm.

19. The layer system according to claim 1, wherein peaks and raised plateaus of the textured surface are spaced apart at different intervals, and wherein some peaks or plateaus are covered by the thin film layer.

20. The layer system according to claim 1, wherein the textured surface contains pyramid top surfaces or pyramid peaks with bases that overlap, and wherein some of the pyramid top surfaces or pyramid peaks are covered by the thin film layer.

21. The layer system according to claim 1, wherein the thin film layer is disposed on a lower portion of the exposed peaks or plateaus.

22. A layered structure having a layer region, the layer region comprising:
   a single-crystal silicon substrate with a front side and a back side;
   a textured surface formed on the front side, the textured surface having a topography with different heights; and
   a thin film layer of a metal oxide and/or an oxide ceramic formed on the textured surface, the thin film layer covering the textured surface only partially,
   wherein a metallically conductive intermediate layer partially or completely covers the textured surface between the thin film layer and the textured surface, and
   wherein the metallic intermediate layer has a texturing with a texture spacing of 0.1 µm to 1 µm and a texture depth of 0.1 µm to 1 µm and the texture spacing and the texture depth are in each case smaller than those at the surface of the silicon substrate.

* * * * *